(12) United States Patent
Foucher et al.

(10) Patent No.: US 6,518,422 B2
(45) Date of Patent: Feb. 11, 2003

(54) PROCESS FOR THE SYNTHESIS OF (3AS)-5, 5-DIOXO-2,3,3A,4-TETRAHYDRO-1H-PYRROLO[2,1-C][1,2,4] BENZOTHIADIAZINE

(75) Inventors: Elsa Foucher, Sausseuzemare-en-Caux (FR); Gilles Thominot, Normanville (FR); Jean-Pierre Lecouve, Le Havre (FR); James Andrew Ramsden, Cambridge (GB); Christopher James Cobley, Cambridge (GB)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 10/125,192

(22) Filed: Apr. 18, 2002

(65) Prior Publication Data
US 2002/0161222 A1 Oct. 31, 2002

(30) Foreign Application Priority Data
Apr. 18, 2001 (FR) ................................ 01 05226

(51) Int. Cl.$^7$ ............................................ C07D 285/20
(52) U.S. Cl. .................................................. 544/9
(58) Field of Search .............................................. 544/9

(56) References Cited

U.S. PATENT DOCUMENTS 3,294,791 A * 12/1966 Wei et al. ....................... 544/9
5,536,719 A * 7/1996 Cordi et al. ................... 544/9

* cited by examiner

*Primary Examiner*—John M. Ford
(74) *Attorney, Agent, or Firm*—The Firm of Hueschen and Sage

(57) ABSTRACT

Process for the industrial synthesis of (3aS)-5,5-dioxo-2,3, 3a,4-tetrahydro-1H-pyrrolo[2,1-c][1,2,4]benzothiadiazine of formula (I):

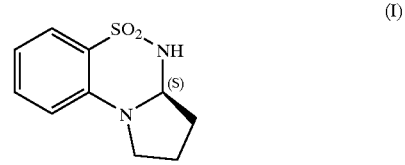

by enantioselective catalytic hydrogenation of 5,5-dioxo-2, 3-dihydro-1H-pyrrolo[2,1-c][1,2,4]benzothiadiazine.

14 Claims, No Drawings

PROCESS FOR THE SYNTHESIS OF (3AS)-5,5-DIOXO-2,3,3A,4-TETRAHYDRO-1H-PYRROLO[2,1-C][1,2,4] BENZOTHIADIAZINE

The present invention relates to a new process for the industrial synthesis of (3aS)-5,5-dioxo-2,3,3a,4-tetrahydro-1H-pyrrolo[2,1-c][1,2,4]benzothiadiazine of formula (I):

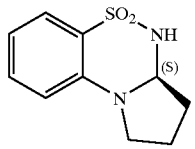
(I)

and addition salts thereof with a pharmaceutically acceptable acid.

BACKGROUND OF THE INVENTION

The compound of formula (I) and salts thereof have powerful activity facilitating the activation caused by glutamic acid at the level of the AMPA receptors, making them useful in the treatment and prevention of pathologies associated with malfunction of glutamatergic neurotransmission, such as disorders of memory and cognition associated with ageing and with syndromes of anxiety and depression, deficiencies of memory in progressive neurodegenerative diseases and also the sequelae of acute neurodegenerative diseases.

DESCRIPTION OF THE PRIOR ART

The compound of formula (I), its use in therapeutics and a preparation method have been described in patent specification EP 0 692 484.

In view of the pharmaceutical interest in this compound and of the fact that only the (S) isomer has facilitatory activity on the AMPA flux, it has been of prime importance to be able to prepare it by an effective synthesis process that allows the (S) isomer to be obtained selectively in a good yield and with excellent purity and that can be readily applied on an industrial scale.

Two methods for the preparation of the compound of formula (I) are known. However, those processes cannot be used on an industrial scale:

Patent specification EP 0 692 484 describes preparation of the compound of formula (I) by non-enantioselective reduction of 5,5-dioxo-2,3-dihydro-1H-pyrrolo[2,1-c][1,2,4]benzothiadiazine using sodium borohydride, followed by separation of the resulting racemic mixture by preparative HPLC chromatography on a chiral phase.

However, this means of separation is not viable on an industrial scale because of its very low productivity.

The publication Bioorg. Med. Chem. Lett. 1996, 6, 3003 describes preparation of the compound of formula (I) by reduction of 5,5-dioxo-2,3-dihydro-1H-pyrrolo[2,1-c][1,2,4]benzothiadiazine using a chiral complex of lithium aluminium hydride. However, the low enantioselectivity of the reduction necessitates laborious enrichment in order to obtain the compound of formula (I) in its optically pure form.

The Applicant has now developed a process for the industrial synthesis of the compound of formula (I) by enantioselective catalytic hydrogenation of 5,5-dioxo-2,3-dihydro-1H-pyrrolo[2,1-c][1,2,4]benzothiadiazine, allowing the (S) isomer to be obtained directly in an excellent yield and with excellent chemical and enantiomeric purity.

DETAILED DESCRIPTION OF THE INVENTION

More specifically, the present invention relates to a process for the industrial synthesis of the compound of formula (I), which process is characterised in that 5,5-dioxo-2,3-dihydro-1H-pyrrolo[2,1-c][1,2,4]benzothiadiazine of formula (II):

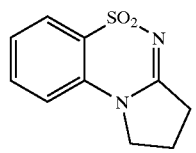
(II)

is hydrogenated in the presence of the catalyst (R)-BINAP $RuCl_2$ (R,R)-DPEN of formula (III):

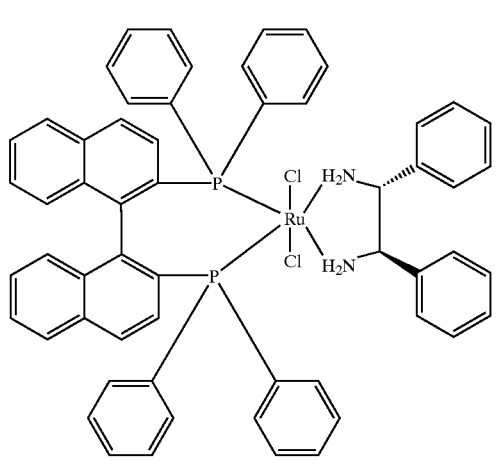
(III)

in a quantity of from 0.4 to 2 mmol per mol of compound of formula (II),
in a mixture of toluene and isopropanol wherein the proportion of toluene is from 10 to 90% by volume, preferably from 70 to 80% by volume,
under hydrogen pressure of from 4 to 25 bar, preferably from 10 to 15 bar,
at a temperature of from 40 to 90° C., preferably from 65 to 75° C.,
and in the presence of a base such as, for example, potassium or sodium tert-butoxide dissolved in an alcoholic solvent such as, for example, tert-butanol or isopropanol, in an amount of from 0.8 to 1.5 mol per mol of compound of formula (I), preferably from 1 to 1.2 mol per mol of compound of formula (I),
to yield directly, after isolation and then recrystallisation, the compound of formula (I) having an enantiomeric excess of more than 80%.

The Example hereinbelow illustrates the invention but does not limit it in any way.

The chemical purity of the compound of formula (I) was determined by HPLC chromatography on a HYPERSIL BDS C18 column, using a mixture of water/acetonitrile 25/75 as eluant.

(Detector: 210 nm; oven: 30° C.; flow rate 1 ml/min)

The enantiomeric purity of the compound of formula (I) was determined by HPLC chromatography on a CHIRAL-PACK AS (Daicel) column, using a mixture of ethanol/heptane 70/30 as eluant.

(Detector: 212 nm; oven: 25° C.; flow rate 1 ml/min)

ABBREVIATIONS

BINAP: 2,2'-(bis(diphenylphosphino))-1,1'-binaphthyl
DPEN: diphenylethylenediamine

EXAMPLE

(3aS)-5,5Dioxo-2,3,3a,4-tetrahydro-1H-pyrrolo[2,1-c][1,2,4]benzothiadiazine

The reaction is carried out in an autoclave.

To 40 g of 5,5-dioxo-2,3-dihydro-1H-pyrrolo[2,1-c][1,2,4]benzothiadiazine dissolved in 450 ml of toluene previously degassed using nitrogen there are added 90.5 mg of catalyst (R)-BINAP RuCl$_2$ (R,R)-DPEN of formula (III) and then a solution, previously heated to 50° C., of potassium tert-butoxide (20.2 g) in isopropanol (150 ml).

After purging with nitrogen, the mixture is heated to 70° C., with stirring, and then 15 bar of hydrogen pressure are applied for 20 hours, whilst still stirring.

After decompression and purging with nitrogen, the reaction mixture is dried, and the residue obtained is then recrystallised from acetone.

The compound of formula (I) is thereby obtained directly in a quantitative yield, having a chemical purity of more than 90% and an enantiomeric excess of 83%.

What is claimed is:

1. A process for the industrial synthesis of (3aS)-5,5-dioxo2,3,3a,4-tetrahydro-1H-pyrrolo[2,1-c][1,2,4]benzothiadiazine of formula (I):

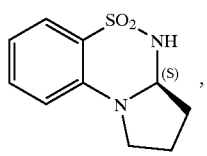

(I)

wherein 5,5-dioxo-2,3dihydro-1H-pyrrolo[2,1-c][1,2,4]benzothiadiazine of formula (II):

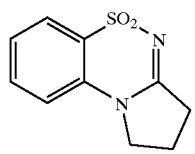

(II)

is hydrogenated in the presence of the catalyst (R)-BINAP RuCl$_2$ (R,R)-DPEN of formula (III):

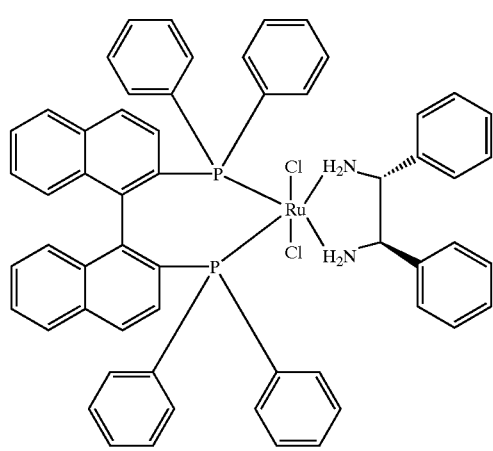

(III)

in an amount of from 0.4 to 2 mmol per mol of compound of formula (II), in a mixture of toluene and isopropanol wherein the proportion of toluene is from 10 to 90% by volume, under hydrogen pressure of from 4 to 25 bar, at a temperature of from 40 to 90° C., and in the presence of a base such as, for example, potassium or sodium tert-butoxide dissolved in an alcoholic solvent such as, for example, tert-butanol or isopropanol, in an amount of from 0.8 to 1.5 mol per mol of compound of formula (I), to yield directly, after isolation and then recrystallisation, the compound of formula (I) having an enantiomeric excess of more than 80%.

2. The process of claim 1, wherein the proportion of toluene in the toluene/isopropanol mixture is from 70 to 80% by volume.

3. The process of claim 1, wherein the hydrogen pressure is from 10 to 15 bar.

4. The process of claim 2, wherein the hydrogen pressure is from 10 to 15 bar.

5. The process of claim 1, wherein the hydrogenation temperature is from 65 to 75° C.

6. The process of claim 2, wherein the hydrogenation temperature is from 65 to 75° C.

7. The process of claim 3, wherein the hydrogenation temperature is from 65 to 75° C.

8. The process of claim 1, wherein the amount of base used is from 1 to 1.2 mol per mol of the compound of formula (I).

9. The process of claim 2, wherein the amount of base used is from 1 to 1.2 mol per mol of the compound of formula (I).

10. The process of claim 3, wherein the amount of base used is from 1 to 1.2 mol per mol of the compound of formula (I).

11. The process of claim 4, wherein the amount of base used is from 1 to 1.2 mol per mol of the compound of formula (I).

12. The process of claim 5, wherein the amount of base used is from 1 to 1.2 mol per mol of the compound of formula (I).

13. The process of claim 6, wherein the amount of base used is from 1 to 1.2 mol per mol of the compound of formula (I).

14. The process of claim 7, wherein the amount of base used is from 1 to 1.2 mol per mol of the compound of formula (I).

* * * * *